US00PP15618P2

(12) United States Plant Patent
Heuger

(10) Patent No.: US PP15,618 P2
(45) Date of Patent: Mar. 1, 2005

(54) *HELLEBORUS* PLANT NAMED 'HGC LADY FRECKLE'

(50) Latin Name: *Helleborus orientalis*
Varietal Denomination: HGC Lady Freckle

(76) Inventor: Joseph Heuger, Münsterstrasse 49, 49129 Glandorf (DE)

( * ) Notice: Subject to any disclaimer, the term of this patent is extended or adjusted under 35 U.S.C. 154(b) by 0 days.

(21) Appl. No.: 10/878,416

(22) Filed: Jun. 28, 2004

(51) Int. Cl.[7] ..... A01H 5/00
(52) U.S. Cl. ..... Plt./263
(58) Field of Search ..... Plt./263

(56) References Cited

PUBLICATIONS

Sunset National Garden Book Mar. 1997, Sunset Books, Menlo Park CA, p. 331.*

UPOV ROM GTITM Computer Database, GTI Jouve Retrieval Software 2004/40 Citation(s) for 'HGC Lady Freckle'.*

Huxley, Anthony, ed. RHS Dictionary of Gardening, vol. 2 D–K. New York: The Stockton Press: 1992. pp. 538–542.*

Wayside Gardens Autumn Catalog 1999; cover, last page and p. 72.*

Seyring, M. In vitro cloning of *Helleborus niger.* Plant Cell Reports 20 (10): p. 895–900 Mar. 2002 (abstract).*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Helleborus* plant named 'HGC Lady Freckle', characterized by its upright and mounded plant habit; dark green-colored leaves; attractive single white-colored flowers with red purple-colored spots; and relatively early flowering.

1 Drawing Sheet

Botanical classification/cultivar designation: *Helleborus orientalis* Hybrid cultivar HGC Lady Freckle.

BACKGROUND OF THE INVENTION

The present Invention relates to a new and distinct cultivar of *Helleborus* plant, botanically known as *Helleborus orientalis* Hybrid, and hereinafter referred to by the cultivar name HGC Lady Freckle.

The new *Helleborus* is a product of a planned breeding program conducted by the Inventor in Glandorf, Germany. The objective of the breeding program was to create new *Helleborus* cultivars with a good plant habit, that flower for a long period of time, and have attractive flower coloration.

The new *Helleborus* originated from a cross-pollination made by the Inventor in January, 1999 in Glandorf, Germany of an unnamed seedling of *Helleborus orientalis* Hybrid, not patented, as the female, or seed, parent with an unnamed seedling of *Helleborus orientalis* Hybrid, not patented, as the male, or pollen, parent. The new *Helleborus* was discovered and selected by the Inventor as a flowering plant within the progeny of the stated cross-pollination in a controlled environment in Glandorf, Germany.

Asexual reproduction of the new cultivar by divisions at Glandorf, Germany since March, 2001, has shown that the unique features of this new *Helleborus* are stable and reproduced true to type in successive generations.

SUMMARY OF THE INVENTION

Plants of the cultivar HGC Lady Freckle have not been observed under all possible environmental conditions. The phenotype may vary somewhat with variations in environment such as temperature and light level without, however, any variance in genotype.

The following traits have been repeatedly observed and are determined to be the unique characteristics of 'HGC Lady Freckle'. These characteristics in combination distinguish 'HGC Lady Freckle' as a new and distinct cultivar of *Helleborus:*

1. Upright and mounded plant habit.
2. Dark green-colored leaves.
3. Attractive single white-colored flowers with red purple-colored spots.
4. Relatively early flowering.

Plants of the new *Helleborus* differed from plants of the parent selections primarily in plant habit.

Plants of the new *Helleborus* can be compared to the *Helleborus niger* cultivar HGC Jericho, disclosed in U.S. Plant Pat. application Ser. No. 10/878,420. In side-by-side comparisons conducted in Glandorf, Germany, plants of the new *Helleborus* differed from plants of the cultivar HGC Jericho in the following characteristics:

1. Plants of the new *Helleborus* were taller and broader than plants of the cultivar HGC Jericho.
2. Plants of the new *Helleborus* had longer leaf petioles than plants of the cultivar HGC Jericho.
3. Plants of the new *Helleborus* had smaller flowers than plants of the cultivar HGC Jericho.
4. Flowers of plants of the new *Helleborus* and the cultivar HGC Jericho differed in coloration as flowers of plants of the new *Helleborus* had red purple-colored spots.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Helleborus*.

The photograph at the top of the sheet comprises a side perspective view of a typical flowering plant of 'HGC Lady Freckle'.

The photograph at the bottom of the sheet is a close-up view of a typical flower of 'HGC Lady Freckle'.

DETAILED BOTANICAL DESCRIPTION

The aforementioned photographs, following observations and measurements describe plants grown in Glandorf, Germany, in a glass-covered greenhouse and under commercial production practices during the winter. Plants were grown in 15-cm containers and were about six months old when the photographs and description were taken. During the production of the plants, day temperatures were about 18° C. and night temperatures were about 14° C. In the following description, color references are made to The Royal Horticultural Society Colour Chart, 1995 Edition, except where general terms of ordinary dictionary significance are used.

Botanical classification: *Helleborus orientalis* Hybrid cultivar HGC Lady Freckle.

Parentage:

*Female parent.*—Unnamed seedling of *Helleborus orientalis* Hybrid, not patented.

*Male parent.*—Unnamed seedling of *Helleborus orientalis* Hybrid, not patented.

Propagation:

*Type.*—By divisions.

*Time to initiate roots, winter.*—About eight weeks at 12° C.

*Time to produce a rooted plant, winter.*—About six months at 12 to 15° C.

*Root description.*—About 3 to 15 thick fleshy roots; not branching; white to brown in color.

Plant description:

*Plant form/habit.*—Upright and mounded plant habit; moderately vigorous growth habit. Leaves basal. Single flower form.

*Plant height.*—About 25 cm.

*Plant width* (*spread*).—About 40 cm.

*Foliage description.*—Arrangement: Basal; palmately compound with five to six leaflets per leaf. Leaflet length: About 6 to 9.5 cm. Leaflet width: About 2.2 to 3.5 cm. Leaflet shape: Lanceolate; pedate. Leaflet apex: Acuminate. Leaflet base: Acute. Leaflet margin: Serrate. Texture, upper and lower surfaces: Smooth, glabrous. Venation pattern: Reticulate. Color: Developing leaflets, upper surface: 137A. Developing leaflets, lower surface: 137C. Fully expanded leaflets, upper surface: 147A. Fully expanded leaflets, lower surface: 147B. Venation, upper and lower surfaces: 146D. Petiole: Length: About 12 cm. Diameter: About 3 mm. Texture, upper and lower surfaces: Smooth, glabrous. Color, upper and lower surfaces: 146B.

Flower description:

*Flower type/habit.*—Single rounded flowers arranged arranged singly on short peduncles; petals inconspicuous; flowers outwardly drooping; typically more than one flowering stem per plant. Freely flowering habit with about 15 flowers developing per plant over the flowering period.

*Fragrance.*—None detected.

*Natural flowering season.*—Relatively early flowering; intermittent flowering from November to February in Glandorf, Germany. Flowers persistent.

*Postproduction longevity.*—Flowers last about ten days on the plant.

*Flower buds.*—Height: About 1.5 cm. Diameter: About 1 cm. Shape: Ovoid. Color: 145C to 145D.

*Flowers.*—Diameter: About 4.5 cm. Depth: About 2.5 cm.

*Petals.*—Size: Minute, obscured by reproductive organs; forming inconspicuous nectaries.

*Sepals.*—Quantity/arrangement per flower: Typically five in a single whorl. Length: About 3 cm. Width: About 3 cm. Shape: Broadly ovate. Apex: Broadly acute. Margin: Entire. Texture, upper and lower surfaces: Smooth, glabrous; satiny. Color: Developing and fully expanded sepals, upper surface: 155C with spots towards the center, 59B. Developing and fully expanded sepals, lower surface: 155C.

*Peduncles.*—Length: About 4.5 cm. Diameter: About 2 mm. Orientation: Bent. Strength: Moderately strong. Texture: Smooth, glabrous. Color: 145A.

*Pedicels.*—None.

*Reproductive organs.*—Stamens: Quantity per flower: About 80. Anther shape: Oblong. Anther length: About 3 mm. Anther color: 145C. Pollen amount: None observed. Pistils: Quantity per flower. About four. Pistil length: About 1.7 cm. Stigma shape: Tuberculate. Stigma color: 145D. Style length: About 5 mm. Style color: 145C to 145D. Ovary color: 145C.

*Seed/fruit.*—Seed and fruit development have not been observed.

Disease/pest resistance: Plants of the new *Helleborus* have not been noted to be resistant to pathogens and pests common to *Helleborus*.

Temperature tolerance: Plants of the new *Helleborus* have been observed to tolerate temperatures from −12 to 36° C.

It is claimed:

1. A new and distinct cultivar of *Helleborus* plant named 'HGC Lady Freckle', as illustrated and described.

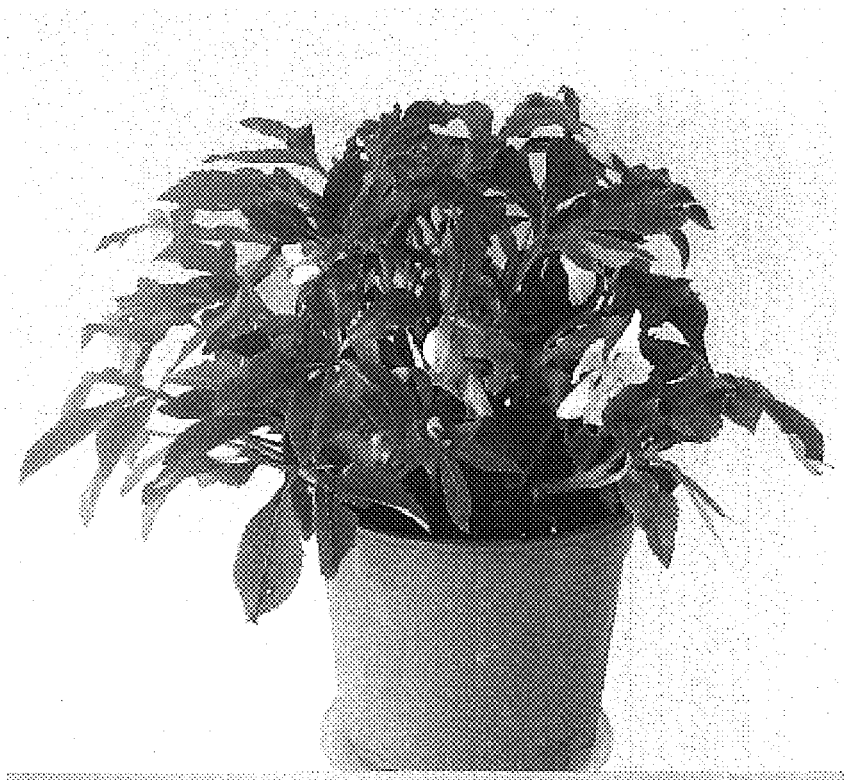
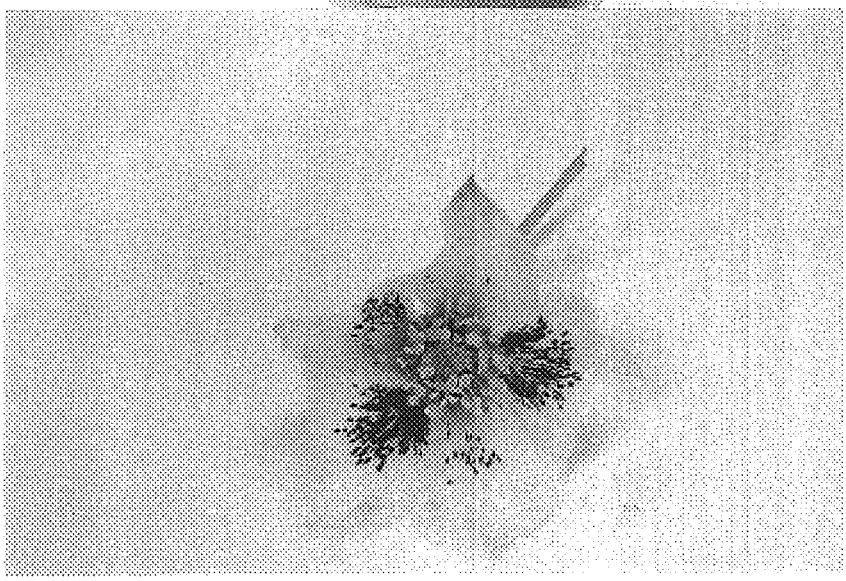

* * * * *